US008293922B2

(12) United States Patent
Kim et al.

(10) Patent No.: US 8,293,922 B2
(45) Date of Patent: Oct. 23, 2012

(54) PROCESSES OF PREPARING GLYCOLURILS AND CUCURBITURILS USING MICROWAVE

(75) Inventors: Kimoon Kim, Pohang (KR); Samal Shashadhar, Pohang (KR); Nandha Kumar Raju, Pohang (KR); Selvapalam Narayanan, Pohang (KR); Dong Hyun Oh, Pohang (KR)

(73) Assignee: Postech Academy-Industry Foundation, Pohang, Kyungsangbuk-do (KR)

( * ) Notice: Subject to any disclaimer, the term of this patent is extended or adjusted under 35 U.S.C. 154(b) by 591 days.

(21) Appl. No.: 11/568,255

(22) PCT Filed: Apr. 26, 2005

(86) PCT No.: PCT/KR2005/001195
§ 371 (c)(1),
(2), (4) Date: Oct. 24, 2006

(87) PCT Pub. No.: WO2005/103053
PCT Pub. Date: Nov. 3, 2005

(65) Prior Publication Data
US 2007/0232809 A1 Oct. 4, 2007

(30) Foreign Application Priority Data
Apr. 26, 2004 (KR) .................. 10-2004-0028626

(51) Int. Cl.
*C07D 403/02* (2006.01)
*C07D 403/04* (2006.01)
(52) U.S. Cl. .................................................. 548/303.4
(58) Field of Classification Search ................ 548/303.4
See application file for complete search history.

(56) References Cited

U.S. PATENT DOCUMENTS 6,365,734 B1  4/2002  Kim et al.

FOREIGN PATENT DOCUMENTS

| DE | 19603377 A1 | 8/1997 |
| EP | 1094065 A2 | 4/2001 |
| JP | 2001-122877 A | 5/2001 |
| JP | 2001-146690 A | 5/2001 |
| JP | 2002-113350 A | 4/2002 |
| JP | 2002-532239 A | 10/2002 |
| JP | 2002-544133 A | 12/2002 |
| JP | 2003-004544 A | 1/2003 |
| JP | 2003-212877 A | 7/2003 |
| JP | 2006-501050 A | 1/2006 |
| WO | 00/36880 A2 | 6/2000 |
| WO | 00/36880 A3 | 6/2000 |
| WO | 00/68232 A1 | 11/2000 |
| WO | 0068232 A1 | 11/2000 |
| WO | 03004500 A1 | 1/2003 |
| WO | 03/055888 A1 | 7/2003 |
| WO | 2004/023144 A1 | 3/2004 |

OTHER PUBLICATIONS

Lagona et al. Angew. Chem. Int. Ed. 2005, 44, 4844-4870.*
Muccioli et al. Tetrahedron 2003, 59, 1301-1307.*
Jon et al. J. Am. Chem. Soc. 2003, 125, 10188-10187.*
Damm et al. J. Comb. Chem. 2009, 11, 460-468.*
D. Bogdal, Chapter 7, Reactions under microwave conditions, in Microwave-assisted Organic Synthesis (2005), pp. 47-190.*
Grillon et al. Tetrahedron Letters 1988, 29(9), 1015-16.*
D. Bogdal, Chapter 2, Microwave effect vs. thermal effect in Microwave-assisted Organic Synthesis (2005), pp. 13-21.*
D.M.P. Mingos, Chapter 1 Theoretical aspects of microwave dielectric heating in Microwave Assisted Organic Synthesis (2005), pp. 1-22, (Tierney & Lidstrom, editors).*
Dariusz Bogdal, Microwave-assisted Organic Synthesis: One Hundred Reaction Procedures (2005), Appendix, References, and Index, 191-202.*
Behrend, et al., "Ueber Condensationsproducte aus Glycoluril und Formaldehyd", Justus Liebig's Annalen Der Chemie, 1905, pp. 1-37.
Freeman, et al., "Cucurbituril", J. Am. Chem. Soc., 1981, vol. 103, pp. 7367-7368.
Kim et al, "New Cucurbituril Homologues: Syntheses, Isoloation Characterization . . . ", J. Am. Chem. Soc., 2000, vol. 122, pp. 540-541.
Day et. al. "Controlling factors in the synthesis of cucurbituril and its homologues", Journal of Organic Chemistry, 2001,66(24), pp. 8094-8100.
Isobe et. al. "Synthesis of disubstituted cucurbit[6]uril and its rotaxane derivative", Organic Letters, 2002, 4(8), pp. 1287-1289.
Jansen et. al. "Glycoluril derivatives as precursors in the preparation of substituted cucurbit[n]urils", Designed Monomers and Polymers, 2003,6(1), pp. 43-55.

* cited by examiner

*Primary Examiner* — Jason M Nolan
(74) *Attorney, Agent, or Firm* — Rothwell, Figg, Ernst & Manbeck, P.C.

(57) ABSTRACT

Provided are processes of preparing glycolurils and cucurbiturils using the glycolurils by microwave irradiation. Therefore, condensation and cyclization reactions for preparation of industrially widely applied cucurbituril derivatives, oxidation reaction for preparation of hydroxycucurbiturils, and condensation and cyclization reactions between glycolurils and paraformaldehyde or a formaldehyde solution can be efficiently performed in a short time.

20 Claims, No Drawings

PROCESSES OF PREPARING GLYCOLURILS AND CUCURBITURILS USING MICROWAVE

CROSS REFERENCE TO RELATED APPLICATION

This application is a 35 U.S.C. §371 National Phase Entry Application from PCT/KR2005/001195, filed Apr. 26, 2005, and designating the U.S.

BACKGROUND OF THE INVENTION

1. Field of the Invention

The present invention relates to processes of preparing glycolurils and cucurbiturils using the glycolurils, and more particularly, to processes of preparing glycolurils and cucurbiturils using the glycolurils by microwave irradiation.

2. Description of the Related Art

Cucurbiturils were first reported by R. Behrend, E. Meyer, and F. Rusche in 1905 [Liebigs Ann. Chem. 1905, 1, 339]. According to their report, first, urea and glyoxal are stirred in the presence of hydrochloric acid (HCl) for two hours to produce glycolurils. The condensation of the glycolurils with excess formaldehyde in the presence of HCl produces an amorphous precipitate. Dissolution of the precipitate in hot concentrated sulfuric acid followed by dilution with water produces a crystalline material. In 1981, W. Mock and his coworkers characterized the crystalline material as a hexameric macrocyclic compound with the composition of $C_{36}H_{36}N_{24}O_{12}$ which was confirmed by X-ray crystal structure determination [J. Am. Chem. Soc. 1981, 103, 7367]. Since then, an improved synthetic method of cucurbit[6]uril has been disclosed (DE 196 03 377 A1). Further, a synthetic method for various cucurbituril homologues under low-temperature reaction conditions has been reported (U.S. Pat. No. 6,365,734). In addition, water-soluble and organic-soluble cucurbiturils and a preparation method thereof have been disclosed (PCT/KR02/01259). According to the preparation method disclosed in this patent application, first, a strong acid solution and glycolurils or their derivatives are added to formaldehyde and incubated at 70-100° C. for 20-40 hours. Then, the reaction solution is concentrated by heating and cooled to room temperature to produce cucurbituril derivatives. As described above, a condensation reaction involved in conventional synthesis of glycolurils and cucurbituril derivatives requires a high reaction temperature and a long reaction time.

SUMMARY OF THE INVENTION

The present invention provides processes of efficiently preparing glycolurils and cucurbiturils using the glycolurils within a short time.

According to an aspect of the present invention, there is provided a process of preparing cucurbituril represented by formula 1 below by irradiating microwave to glycoluril represented by formula 2 below and paraformaldehyde or a formaldehyde solution in the presence of an acid catalyst:

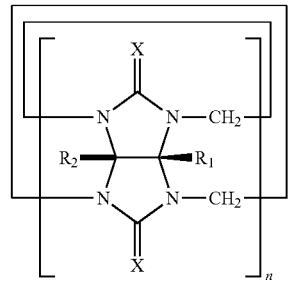
(1)

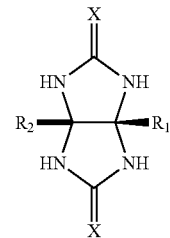
(2)

wherein X is O, S, or NH;

$R_1$ and $R_2$ are each independently selected from the group consisting of hydrogen, a substituted or unsubstituted alkyl group of C1-C30, a substituted or unsubstituted alkenyl group of C2-C30, a substituted or unsubstituted alkynyl group of C2-C30, a substituted or unsubstituted alkylcarboxyl group of C2-C30, a substituted or unsubstituted hydroxyalkyl group of C1-C30, a substituted or unsubstituted alkoxy group of C1-C30, a substituted or unsubstituted nitroalkyl group of C1-C30, —N(R')(R") where R' and R" are each independently hydrogen or an alkyl group of C1-C30, a substituted or unsubstituted cycloalkyl group of C5-C30, a substituted or unsubstituted heterocycloalkyl group of C2-C30, a substituted or unsubstituted aryl group of C6-C30, and a substituted or unsubstituted heteroaryl group of C2-C30; and n is an integer from 4 to 20.

According to another aspect of the present invention, there is provided a process of preparing hydroxycucurbituril represented by formula 5 below by irradiating microwave to cucurbituril represented by formula 1 below in the presence of an oxidizing agent:

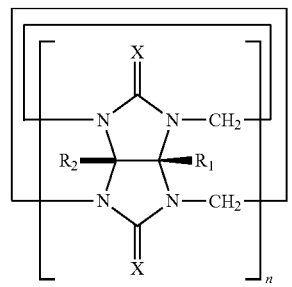
(1)

-continued

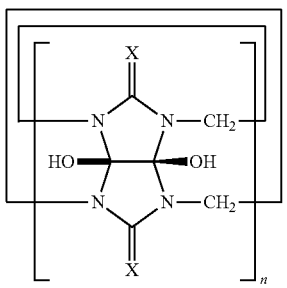

(5)

wherein $R_1$ and $R_2$ are hydrogen; X is O, S, or NH; and n is an integer from 4 to 20.

According to still another aspect of the present invention, there is provided a process of preparing disubstituted cucurbituril represented by formula 7 below, the process including: mixing disubstituted glycoluril represented by formula 6 below and glycoluril represented by formula 8 below with paraformaldehyde or a formaldehyde solution and irradiating microwave to the resultant mixture in the presence of an acid catalyst:

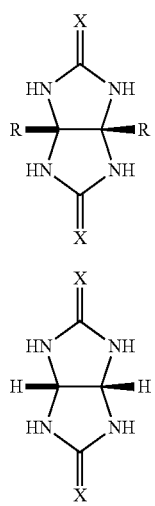

(6)

(8)

(7)

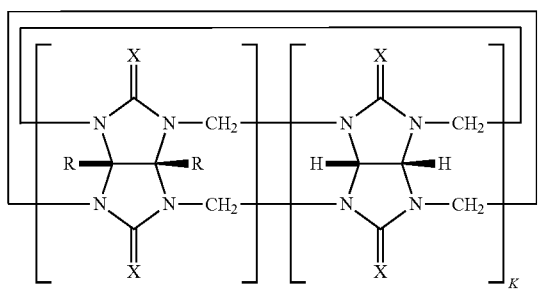

wherein R is selected from the group consisting of hydrogen, a substituted or unsubstituted alkyl group of C1-C30, a substituted or unsubstituted alkenyl group of C2-C30, a substituted or unsubstituted alkynyl group of C2-C30, a substituted or unsubstituted alkylcarboxyl group of C2-C30, a substituted or unsubstituted hydroxyalkyl group of C1-C30, a substituted or unsubstituted alkoxy group of C1-C30, a substituted or unsubstituted nitroalkyl group of C1-C30, —N(R')(R'') where R' and R'' are each independently hydrogen or an alkyl group of C1-C30, a substituted or unsubstituted cycloalkyl group of C5-C30, a substituted or unsubstituted heterocycloalkyl group of C2-C30, a substituted or unsubstituted aryl group of C6-C30, and a substituted or unsubstituted heteroaryl group of C2-C30;

X is O, S, or NH; and k is an integer from 4 to 7.

According to yet another aspect of the present invention, there is provided a process of preparing glycoluril represented by formula 2 below by irradiating microwave to a 1,2-diketone compound represented by formula 3 below and an urea compound represented by formula 4 below in the presence of an acid catalyst:

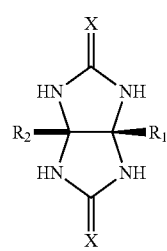

(2)

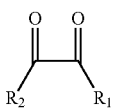

(3)

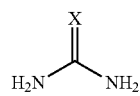

(4)

wherein X is O, S, or NH; and $R_1$ and $R_2$ are each independently selected from the group consisting of hydrogen, a substituted or unsubstituted alkyl group of C1-C30, a substituted or unsubstituted alkenyl group of C2-C30, a substituted or unsubstituted alkynyl group of C2-C30, a substituted or unsubstituted alkylcarboxyl group of C2-C30, a substituted or unsubstituted hydroxyalkyl group of C1-C30, a substituted or unsubstituted alkoxy group of C1-C30, a substituted or unsubstituted nitroalkyl group of C1-C30, —N(R')(R'') where R' and R'' are each independently hydrogen or an alkyl group of C1-C30, a substituted or unsubstituted cycloalkyl group of C5-C30, a substituted or unsubstituted heterocycloalkyl group of C2-C30, a substituted or unsubstituted aryl group of C6-C30, and a substituted or unsubstituted heteroaryl group of C2-C30.

The microwave irradiation may be performed at a power level of 300 to 1,600 W for 30 seconds to 10 minutes. The acid catalyst may be one or more selected from the group consisting of hydrochloric acid, sulfuric acid, trifluoroacetic acid, methanesulfonic acid, phosphoric acid, tetrafluoroboric acid and toluenesulfonic acid.

According to yet another aspect of the present invention, there is a process of preparing cucurbituril represented by formula 11 below by irradiating microwave to glycoluril represented by formula 10 below and paraformaldehyde or a formaldehyde solution in the presence of an acid catalyst:

(11)

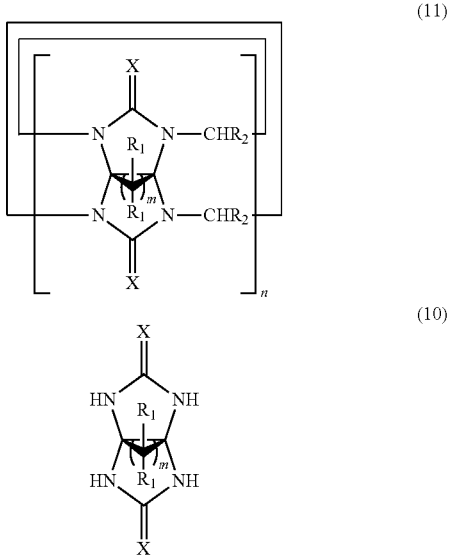

(10)

where X is O, S or NH; $R_1$ and $R_2$ are independently selected from the group consisting of hydrogen, alkyl groups of 1 to 30 carbon atoms, alkenyl groups of 1 to 30 carbon atoms, alkynyl groups of 1 to 30 carbon atoms, alkylthio groups of 1 to 30 carbon atoms, alkylcarboxyl groups of 1 to 30 carbon atoms, hydroxyalkyl groups of 1 to 30 carbon atoms, alkylsilyl groups of 1 to 30 carbon atoms, alkoxy groups of 1 to 30 carbon atoms, haloalkyl groups of 1 to 30 carbon atoms, nitro group, alkylamine groups of 1 to 30 carbon atoms, amine group, aminoalkyl groups of 1 to 30 carbon atoms, unsubstituted cycloalkyl groups of 5 to 30 carbon atoms, cycloalkyl groups of 4 to 30 carbon atoms with hetero atoms, unsubstituted aryl groups of 6 to 30 carbon atoms, and aryl groups of 6 to 30 carbon atoms with hetero atoms; and n and m are independently integers from 4 to 20 and from 1 to 7, respectively.

DETAILED DESCRIPTION OF THE INVENTION

Hereinafter, the present invention will be described in more detail.

The present invention provides processes of efficiently preparing industrially widely used cucurbiturils in a short time by using microwave irradiation for condensation and cyclization reactions in the preparation of cucurbituril derivatives, for oxidation reaction in the preparation of hydroxycucurbiturils, and for condensation and cyclization reactions between glycolurils and paraformaldehyde or a formaldehyde solution.

As used herein, the term "microwave" indicates an electronic spectrum range with a frequency of 30 GHz to 300 MHz corresponding to a wavelength of 1 cm to 1 m. To avoid an interference with laser wavelength, it is required that domestic or industrial microwave radiators are operated at a wavelength of 12.2 cm (corresponding to a frequency of 2.45 GHz) or at a wavelength of 33.3 cm (corresponding to a frequency of 918 MHz). In this regard, in exemplary embodiments of the present invention, the term "microwave" refers to the above wavelength. Common microwave equipment may be used in preparation processes according to the present invention.

The present invention provides a process of preparing cucurbituril represented by formula 1 below by microwave irradiation:

(1)

wherein X is O, S, or NH; $R_1$ and $R_2$ are each independently selected from the group consisting of hydrogen, a substituted or unsubstituted alkyl group of C1-C30, a substituted or unsubstituted alkenyl group of C2-C30, a substituted or unsubstituted alkynyl group of C2-C30, a substituted or unsubstituted alkylcarboxyl group of C2-C30, a substituted or unsubstituted hydroxyalkyl group of C1-C30, a substituted or unsubstituted alkoxy group of C1-C30, a substituted or unsubstituted nitroalkyl group of C1-C30, —N(R')(R") where R' and R" are each independently hydrogen or an alkyl group of C1-C30, a substituted or unsubstituted cycloalkyl group of C5-C30, a substituted or unsubstituted heterocycloalkyl group of C2-C30, a substituted or unsubstituted aryl group of C6-C30, and a substituted or unsubstituted heteroaryl group of C2-C30; and n is an integer from 4 to 20.

The cucurbituril of formula 1 is obtained by condensation and cyclization reactions between glycoluril represented by formula 2 and paraformaldehyde or a 37% formaldehyde solution in the presence of an acid catalyst under microwave irradiation, as represented by reaction scheme 1:

<Reaction Scheme 1>

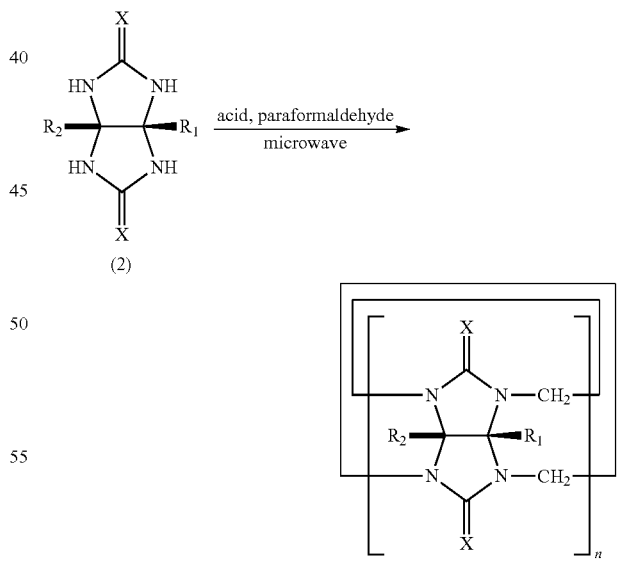

wherein X, $R_1$, $R_2$, and n are as defined above.

The microwave irradiation may be performed at a power level of 300 to 1,600 W, preferably 600 to 850 W, and particularly preferably about 800 W. The duration for the microwave irradiation may vary according to conditions such as the amount of reactants but may be in the range from 20 seconds to 10 minutes, preferably from 30 seconds to 7 minutes. As described above, according to the present invention, cucurbiturils can be prepared within a very short time, i.e., several seconds to several minutes, by microwave irradiation, unlike conventional techniques requiring about 24-50 hours for preparation of cucurbiturils.

The acid catalyst may be one or more selected from the group consisting of hydrochloric acid, sulfuric acid, trifluoroacetic acid, methanesulfonic acid, phosphoric acid, tetrafluoroboric acid and toluenesulfonic acid. The content of the paraformaldehye or the formaldehyde may be in the range from 1 to 1.5 moles based on 1 mole of the glycoluril of formula 2.

In the cucurbituril of formula 1 obtained according to the above-described process, it is preferable that X is O, $R_1$ and $R_2$ are hydrogen, and n is an integer from 5 to 8.

Preferably, the glycoluril of formula 2 is glycoluril represented by formula 9 below where X is O, $R_1$ and $R_2$ are hydrogen:

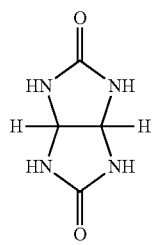

(9)

The glycoluril of formula 2 is obtained through condensation reaction between a 1,2-diketone compound represented by formula 3 and an urea compound represented by formula 4 in the presence of an acid catalyst under microwave irradiation as illustrated in reaction scheme 2:

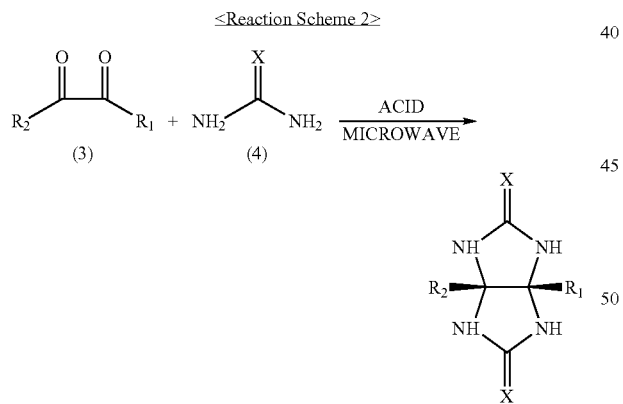

<Reaction Scheme 2> wherein $R_1$, $R_2$, and X are as defined above.

The microwave irradiation may be performed at a power level of 300 to 1,600 W, preferably 600 to 850 W, and particularly preferably about 800 W. The duration for the microwave irradiation may vary according to conditions such as the amount of products but may be in the range from 30 seconds to 7 minutes, preferably 30 seconds to 1 minute. In this way, according to the present invention, glycolurils can be prepared within a very short time, i.e., several seconds to several minutes, by microwave irradiation, unlike conventional techniques requiring about 2 hours or more (at 70-80° C.) for preparation of glycolurils.

In the preparation of glycolurils, the content of the urea compound may be in the range from 2 to 3 moles based on 1 mole of the 1,2-diketone compound. The acid catalyst may be one or more selected from the group consisting of hydrochloric acid, sulfuric acid, trifluoroacetic acid, methanesulfonic acid, phosphoric acid, tetrafluoroboric acid and toluenesulfonic acid. Hydrochloric acid is preferred. The content of the acid catalyst may be in the range from 1 to 3 moles based on 1 mole of the 1,2-diketone compound.

The present invention also provides a process of preparing hydroxycucurbituril represented by formula 5 by dissolving cucurbituril represented by formula 1 below in water, followed by microwave irradiation in the presence of an oxidizing agent, as illustrated in reaction scheme 3:

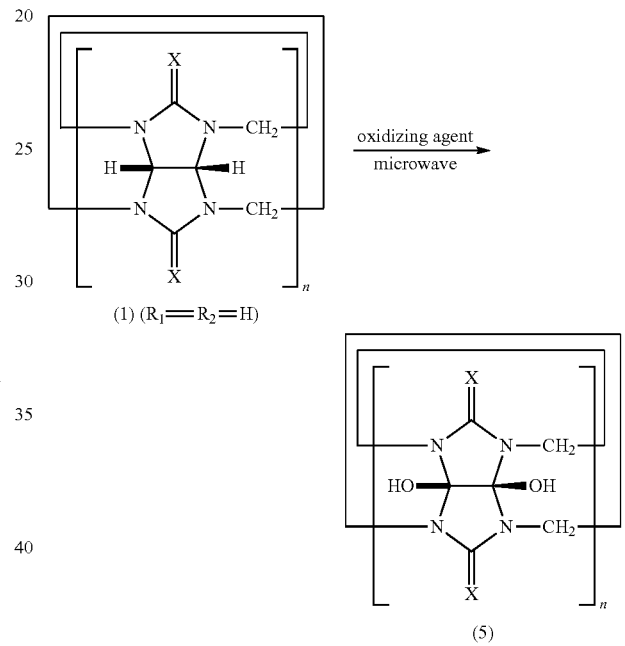

<Reaction Scheme 3> wherein X and n are as defined above.

The microwave irradiation may be performed at a power level of 300 to 1,600 W, preferably 800 W, for 30 seconds to 10 minutes, preferably 1 to 5 minutes.

The oxidizing agent may be at least one selected from the group consisting of $K_2S_2O_8$, $(NH_4)_2S_2O_8$, and $Na_2S_2O_8$. The content of the oxidizing agent may be in the range from 2*n to 2.2*n moles based on 1 mole of cucurbit[n]uril as represented by formula 1. The content of water used to dissolve the cucurbituril of formula 1 may be in the range from 2,000 to 4,000 parts by weight based on 100 parts by weight of the cucurbituril of formula 1.

The present invention also provides a process of preparing disubstituted cucurbituril represented by formula 7 below, which includes: mixing glycoluril represented by formula 8 below and disubstituted glycoluril represented by formula 6 below in a predetermined ratio, mixing the mixture with paraformaldehyde or a formaldehyde solution, and irradiating microwave to the resultant mixture in the presence of an acid catalyst, which is represented in reaction scheme 4:

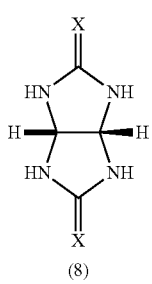

(8)

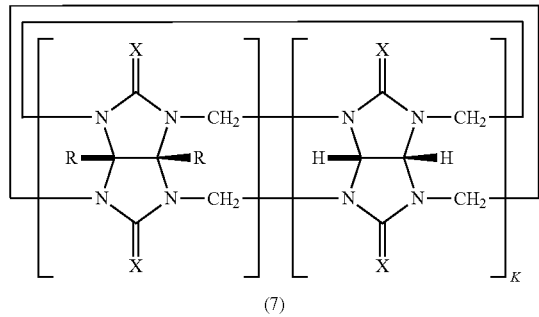

(7)

<Reaction Scheme 4>

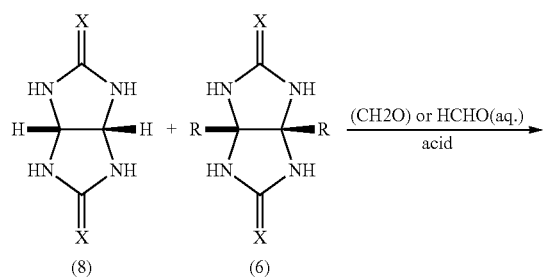

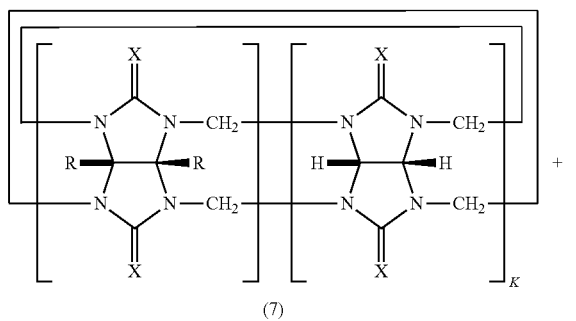

wherein X, R, and k are as defined above.

The above reaction for preparation of disubstituted cucurbituril is performed within a short time by microwave irradiation, unlike conventional methods requiring stirring for more than several tens hours for preparation of disubstituted cucurbiturils. The microwave irradiation may be performed using a microwave oven.

The microwave irradiation may be performed at a power level of 300 to 1,600 W, preferably 800 W, for 10 seconds to 10 minutes, preferably 1 to 7 minutes.

With respect to preparation of disubstituted cucurbit[m]uril (m=k+1, 5 to 8), the glycoluril of formula 8 is used in an amount of k to 1.2 k moles, i.e., 4 to 7.2 moles, based on 1 mole of the disubstituted glycoluril of formula 6. For example, when k is 5, the glycoluril of formula 8 is used in an amount of 5 to 5.2 moles based on 1 mole of the disubstituted glycoluril of formula 6. The acid catalyst may be one or more selected from the group consisting of hydrochloric acid, sulfuric acid, trifluoroacetic acid, methanesulfonic acid, phosphoric acid, tetrafluoroboric acid and toluenesulfonic acid. An excess of the acid catalyst relative to cucurbituril is used. In detail, the acid catalyst is used in an amount of 2 to 50 times of the weight of cucurbituril. The content of the formaldehyde or the paraformaldehyde is in the range from 1 to 1.5 moles based on 1 mole of the disubstituted glycoluril of formula 6.

After the reaction is terminated, disubstituted cucurbituril can be obtained by the work-up of the reaction mixture. At this time, the work-up of the reaction mixture is not particularly limited but may be recrystallization with acetone and water. In more detail, the reaction mixture is left behind at room temperature for 1-20 hours to form a cucurbituril precipitate. The precipitate is primarily filtered. Acetone is added to the resulting filtrate to form a precipitate. The precipitate is washed several times with a mixed solvent of acetone and water (mixture ratio: 2:1-10:1, v/v) and dried to thereby complete the production of a desired disubstituted cucuribituril.

In the disubstituted cucurbituril of formula 7 prepared according to the above preparation method, it is preferable that X is O, R is selected from the group consisting of 2-nitrophenyl group, 3-nitrophenyl group, 4-nitrophenyl group, 2-methoxyphenyl group, 3-methoxyphenyl group, 4-methoxyphenyl group, 2-aminophenyl group, 3-aminophenyl group, 4-aminophenyl group, 2-hydroxyphenyl group, 3-hydroxyphenyl group, and 4-hydroxyphenyl group, and k is an integer from 4 to 7.

Also, the present invention provides a process of preparing cucurbituril represented by the formula 11.

The cucurbituril of formula 11 is obtained by condensation and cyclization reactions between glycoluril represented by formula 10 and paraformaldehyde or a 37% formaldehyde solution in the presence of an acid catalyst under microwave irradiation, as represented by reaction scheme below.

<Reaction Scheme 5>

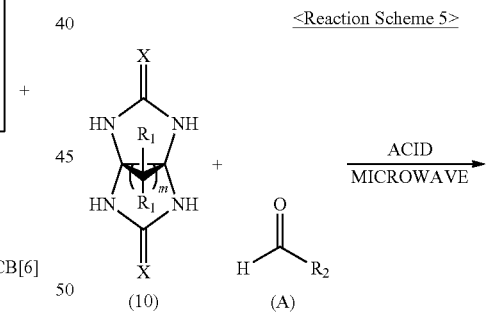

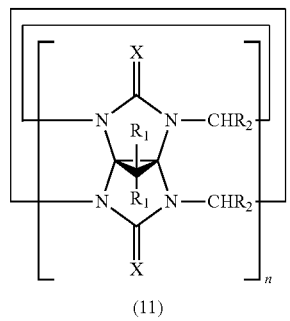

(11)

wherein X, $R_1$, $R_2$, and n are as defined above.

The microwave irradiation may be performed at a power level of 300 to 1,600 W, preferably 600 to 850 W, and particularly preferably about 800 W. The duration for the microwave irradiation may vary according to conditions such as the amount of reactants but may be in the range from 20 seconds to 10 minutes, preferably from 30 seconds to 7 minutes. As described above, according to the present invention, cucurbiturils can be prepared within a very short time, i.e., several seconds to several minutes, by microwave irradiation, unlike conventional techniques requiring about 24-50 hours for preparation of the above cucurbiturils.

The acid catalyst may be one or more selected from the group consisting of hydrochloric acid, sulfuric acid, trifluoroacetic acid, methanesulfonic acid, phosphoric acid, tetrafluoroboric acid and toluenesulfonic acid. The content of the paraformaldehye or the formaldehyde may be in the range from 1 to 1.5 moles based on 1 mole of the glycoluril of formula 10.

The alkyl groups of 1 to 30 carbon atoms for $R_1$ and $R_2$ of formula 11 may include methyl, ethyl, propyl, isopropyl and t-butyl groups. The alkenyl groups of 1 to 30 carbon atoms for $R_1$ and $R_2$ may include propylene and butene groups, and the alkynyl groups of 1 to 30 carbon atoms therefore may include a hexynyl group. The alkylthio groups of 1 to 30 carbon atoms may include butylmethylsulfide and octanethiol groups. The alkylcarboxyl groups of 1 to 30 carbon atoms may include carboxypropyl and carboxylbutyl groups. The hydroxylalkyl groups of 1 to 30 carbon atoms may include hydroxybutyl and hydroxyethyl groups. The alkylsilyl groups of 1 to 30 carbon atoms may include aryltriethylsilyl and vinyltriethylsilyl groups, and the alkoxy groups of 1 to 30 carbon atoms may include methoxy and ethoxy groups. The haloalkyl groups of 1 to 30 carbon atoms may include $CF_3$ and $CH_2Cl$, the alkylamine groups of 1 to 30 carbon atoms may include methylamine and ethylamine groups, and the aminoalkyl groups of 1 to 30 carbon atoms may include 2-aminobutyl and 1-aminobutyl groups. The unsubstituted cycloalkyl groups of 5 to 30 carbon atoms may include cyclohexyl and cyclopentyl groups, and the cycloalkyl groups of 4 to 30 carbon atoms with hetero atoms may include piperidyl and tetrahydrofuranyl groups. The unsubstituted aryl groups of 6 to 30 carbon atoms may include phenyl, benzyl and naphthyl groups, and the aryl groups of 6 to 30 carbon atoms with hetero atoms may include pentafluorophenyl and pyridyl groups.

As described above, in the present invention, four organic reactions, i.e., condensation reaction between urea and 1,2-diketone for glycoluril synthesis, condensation reaction between glycoluril and paraformaldehyde for cucurbituril derivative synthesis, condensation reaction between substituted glycoluril and paraformaldehyde for cucurbituril derivative synthesis and oxidation reaction of cucurbituril for hydroxycucurbituril synthesis, can be efficiently performed in a shorter time by microwave irradiation than conventional thermal-treatment techniques requiring a long reaction time.

In R groups as used herein, the term "heteroaryl" means an aromatic group which contains 1, 2, or 3 hetero atoms selected from N, O, P and S, and the remaining ring atoms of which are carbon. The term "heteroaryl" also means an aromatic group forming N-oxide or a quaternary salt by oxidation or quaternization of a heteroatom in the ring. Examples of such heteroaryl include thienyl, benzothienyl, pyridyl, pyrazinyl, pyrimidinyl, pyridazinyl, quinolinyl, quinoxalinyl, imidazolyl, furanyl, benzofuranyl, thiazolyl, isoxazolyl, benzisoxazolyl, benzimidazolyl, triazolyl, pyrazolyl, pyrrolyl, indolyl, 2-pyridonyl, 4-pyridonyl, N-alkyl-2-pyridonyl, pyrazinonyl, pyridazinonyl, pyrimidinonyl, oxazolonyl, and their equivalent N-oxides (e.g., pyridyl N-oxide or quinolinyl N-oxide), and quaternary salts thereof.

In formula 1, one or more hydrogen atoms on the alkyl group of C1-C30, the alkenyl group of C2-C30, the alkynyl group of C2-C30, the alkylcarboxyl group of C2-C30, the hydroxyalkyl group of C1-C30, the alkoxy group of C1-C30, the nitroalkyl group of C1-C30, the cycloalkyl group of C5-C30, the heterocycloalkyl group of C2-C30, the aryl group of C6-C30, and the heteroaryl group of C2-C30 may be substituted by a halogen atom, halide, a hydroxy group, a nitro group, an alkoxy group, a cyano group, a substituted or unsubstituted amino group, a carboxyl group, a sulfonic acid group, an alkyl group of C1-C10, or an aryl group of C6-C15.

Hereinafter, the present invention will be described more specifically with reference to the following examples. The following examples are for illustrative purposes and are not intended to limit the scope of the invention.

Example 1

Synthesis of Glycolurils 6.84 g of urea and 1 mL of concentrated HCl were added to 5 mL of glyoxal in a reactor and a 800 W microwave was irradiated to the reaction mixture for 15 seconds.

The resultant solid in the reactor was washed several times with water and dried to give glycolurils (yield: 85%) of formula 9 below:

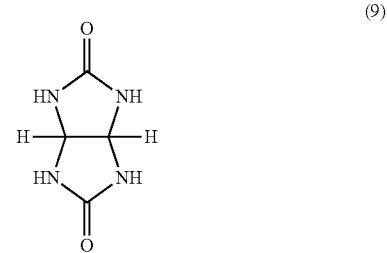

(9)

$^1$H-NMR (500 MHz, $D_2O$): =5. 33(s, 2H), 7.28 (s, 4H).

Example 2

Synthesis of Cucurbituril Homologues 3 g of paraformaldehyde was added to 5.68 g of glycolurils of formula 9 and 20 mL of a 9M sulfuric acid was added thereto. Then, a 800 W microwave was irradiated to the reaction mixture for 45 seconds.

The reaction solution was recrystallized with acetone and methanol to thereby synthesize and separate four cucurbituril homologues, CB[5], CB[6], CB[7], and CB[8], as represented by formula 1 where X is O, R1 and R2 are H, and n is 5, 6, 7, and 8, respectively. The yields of CB[5], CB[6], CB[7], and CB[8] were 15%, 45%, 20%, and 15%, respectively.

CB[5]: 1H NMR (500 MHz, $D_2O$/CF3CO2D/D2SO4 (1:1: 0.15)): δ 4.43 (d, J=15.5 Hz, 10H), 5.65 (s, 10H), 5.85 (d, J=15.5 Hz, 10H).

CB[6]: 1H NMR (500 MHz, $D_2O$/CF3CO2D/D2SO4 (1:1: 0.15)): δ 4.35 (d, J=15.5 Hz, 12H), 5.61 (s, 12H), 5.69 (d, J=15.5 Hz, 12H).

CB[7]: 1H NMR (500 MHz, $D_2O$/CF3CO2D/D2SO4 (1:1: 0.15)): δ 4.29 (d, J=15.5 Hz, 14H), 5.60 (s, 14H), 5.91 (d, J=15.5 Hz, 14H).

CB[8]: 1H NMR (500 MHz, D$_2$O/CF3CO2D/D2SO4 (1:1: 0.15)): δ 4.28 (d, J=15.5 Hz, 16H), 5.60 (s, 16H), 5.93 (d, J=15.5 Hz, 16H).

Example 3

Synthesis of metadinitrophenylcucurbiturils 3.84 g of glycolurils of formula 2 where R1 and R2 are metanitrophenyl and X is O, 7.14 g of glycolurils of formula 8, and 4.6 g of paraformaldehyde were placed in a reactor. Then, 27 mL of a 12M sulfuric acid was gradually added to the reaction mixture and a 800 W microwave was irradiated thereto for 5 minutes.

The reaction solution was left behind at room temperature for 3 hours. The precipitated cucurbit[6]urils were filtered with a filter paper. Acetone was added to the filtrate to thereby produce a precipitate. The precipitate was washed with acetone and water (5:1 volumetric ratio give metadinitrophenylcucurbit[6]urils (k=5) (yield: 17%) of formula 7 where R1 and R2 are metanitrophenyl and X is O.

1H NMR (500 MHz, D$_2$O): δ 4.40 (m, 12H), 5.27 (d, J=10.0, 2H), 5.57 (d, J=10.0 Hz, 2H), 5.71 (m, 6H), 5.81 (m, 8H), 6.10 (m, 4H), 7.49 (m, 4H), 7.89 (d, J=25.0 Hz, 2H), 8.03 (m, 2H).

Example 4

Synthesis of hydroxycucurbiturils 39 g of K2S2O8 used as an oxidizing agent was added to 10 g of cucurbiturils of formula 1 where X is O, n is 6, R1 and R2 are H. Then, 25 mL of water was added to the reaction mixture and a 800 W microwave was irradiated thereto for 5 minutes.

After the reaction was terminated, the filtrate was collected and acetone was added to the filtrate to give hydroxycucurbiturils (yield: 45%) of formula 5 where X is O and n is 6.

1H NMR (500 MHz, D$_2$O): δ 4.42 (d, J=10.0 Hz, 2H), 5.67 (d, J=10.0 Hz, 2H), 7.98 (s).

Example 5

Synthesis of decamethylcucurbiturils 320 mg of dimethylglycolurils of formula 2 where X is O, R1 and R2 are methyl, were dissolved in 10 mL of a 9M sulfuric acid solution and then 100 mg of paraformaldehyde was added thereto. A 800 W microwave was then irradiated to the reaction mixture for 50 seconds.

After the reaction was terminated, the filtrate was collected and washed with acetone and water to give decamethylcucurbiturils (yield: 16%) of formula 5 where X is O, R1 and R2 are methyl, and n is 5.

1H NMR (500 MHz, D$_2$O): δ1.69 (s, 30H), 4.33 (d, J=16.0 Hz, 10H), 5.32 (d, J=16.0 Hz, 10H).

Example 6

Synthesis of Substituted cucurbituril Derivative Having the Formula (1) Where n=5 and 6, m=4, X=O, R$_1$=R$_2$=H

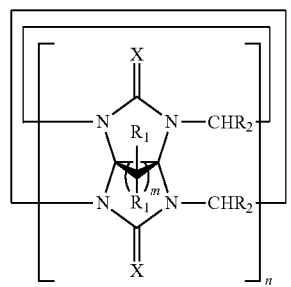

(11)

1.9 ml of a 30% formaldehyde aqueous solution and 2.0 g of the glycoluril derivative having the formula (2) with m=4, X=O and R1=H, were mixed and 0.16 ml of 37% aqueous hydrochloric acid solution was added thereto. Then, 5 ml of water and 2.5 ml of sulfuric acid were added and a 800 W microwave was then irradiated to the reaction mixture for 50 seconds. After the reaction was completed, the resultant product (resulting solution) was cooled to room temperature and diluted with 10 ml of water. Then, 300 ml of acetone was added to the reaction mixture to form a precipitate. The obtained precipitate was filtered, washed with acetone and recrystallized with water or a mixture of water and acetone to give colorless crystalline cucurtbituril derivatives, where n=5, m=4, X=O and R1=R2=H (to be termed "CB*[5]") in a yield of 40% and where n=6, m=4, X=O and R1=R2=H (to be termed "CB*[6]") in a yield of 10%.

where n=5, m=4, X=O, R1=R2=H

1H NMR (300 MHz, D$_2$O): δ=5.64 (d, J=15.6 Hz, 10H), 4.33 (d, J=15.8 Hz, 10H), 2.20 (s, 20H), 1.46 (s, 20H);

where n=6, m=4, X=O, R1=R2=H

1H NMR (300 MHz, D$_2$O): δ=5.73 (d, J=15.9 Hz, 12H), 4.32 (d, J=16.0 Hz, 12H), 2.26 (s, 24H), 1.49 (s, 24H);

According to the present invention, condensation and cyclization reactions for preparation of industrially widely applied cucurbituril derivatives, oxidation reaction for preparation of hydroxycucurbiturils, and condensation and cyclization reactions between glycolurils and paraformaldehyde or a formaldehyde solution can be efficiently performed in a short time.

The invention claimed is:

1. A process of preparing cucurbituril represented by formula 1 below by irradiating microwave to glycoluril represented by formula 2 below and paraformaldehyde or a formaldehyde solution in the presence of an acid catalyst, wherein the microwave is irradiated at a power level of 300 to 1,600 W:

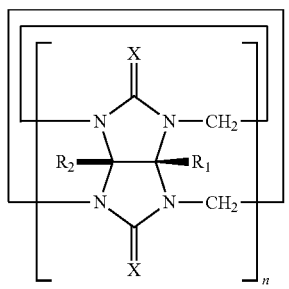

(1)

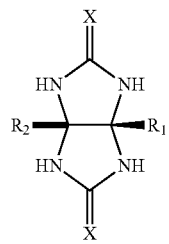

(2)

wherein X is O, S, or NH;

$R_1$ and $R_2$ are each independently selected from the group consisting of hydrogen, a substituted or unsubstituted alkyl group of C1-C30, a substituted or unsubstituted alkenyl group of C2-C30, a substituted or unsubstituted alkynyl group of C2-C30, a substituted or unsubstituted alkylcarboxyl group of C2-C30, a substituted or unsubstituted hydroxyalkyl group of C1-C30, a substituted or unsubstituted alkoxy group of C1-C30, a substituted or unsubstituted nitroalkyl group of C1-C30, —N(R')(R") where R' and R" are each independently hydrogen or an alkyl group of C1-C30, a substituted or unsubstituted cycloalkyl group of C5-C30, a substituted or unsubstituted heterocycloalkyl group of C2-C30, a substituted or unsubstituted aryl group of C6-C30, and a substituted or unsubstituted heteroaryl group of C2-C30; and n is an integer from 5 to 8, or 10.

2. The process of claim 1, wherein the glycoluril represented by the formula 2 is obtained by irradiating microwave to a 1,2-diketone compound represented by formula 3 below and an urea compound represented by formula 4 below in the presence of an acid catalyst:

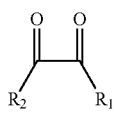

(3)

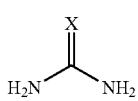

(4)

wherein $R_1$ and $R_2$ are each independently selected from the group consisting of hydrogen, a substituted or unsubstituted alkyl group of C1-C30, a substituted or unsubstituted alkenyl group of C2-C30, a substituted or unsubstituted alkynyl group of C2-C30, a substituted or unsubstituted alkylcarboxyl group of C2-C30, a substituted or unsubstituted hydroxyalkyl group of C1-C30, a substituted or unsubstituted alkoxy group of C1-C30, a substituted or unsubstituted nitroalkyl group of C1-C30, —N(R')(R") where R' and R" are each independently hydrogen or an alkyl group of C1-C30, a substituted or unsubstituted cycloalkyl group of C5-C30, a substituted or unsubstituted heterocycloalkyl group of C2-C30, a substituted or unsubstituted aryl group of C6-C30, and a substituted or unsubstituted heteroaryl group of C2-C30; and X is O, S, or NH.

3. The process of claim 1, wherein the microwave is irradiated for 30 seconds to 10 minutes.

4. The process of claim 1, wherein the acid catalyst is at least one selected from the group consisting of hydrochloric acid, sulfuric acid, trifluoroacetic acid, methanesulfonic acid, phosphoric acid, tetrafluoroboric acid and toluenesulfonic acid.

5. The process of claim 1, wherein in the cucurbituril represented by the formula 1, X is O, $R_1$ and $R_2$ are hydrogen, and n is an integer from 5 to 8.

6. The process of claim 1, wherein in the glycoluril represented by the formula 2, X is O, $R_1$ and $R_2$ are hydrogen.

7. A process of preparing hydroxycucurbituril represented by formula 5 below by irradiating microwave to cucurbituril represented by formula 1 below in the presence of an oxidizing agent, wherein the microwave is irradiated at a power level of 300 to 1,600 W:

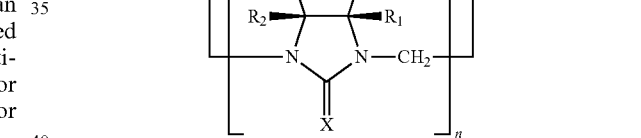

(1)

(5)

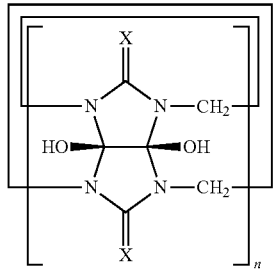

wherein $R_1$ and $R_2$ are hydrogen, X is O, S, or NH, and n is an integer from 5 to 8, or 10.

8. The process of claim 7, wherein the microwave is irradiated for 30 seconds to 10 minutes.

9. The process of claim 7, wherein the oxidizing agent is at least one selected from the group consisting of $K_2S_2O_8$, $(NH_4)_2S_2O_8$, and $Na_2S_2O_8$.

10. A process of preparing disubstituted cucurbituril represented by formula 7 below, the process comprising: mixing disubstituted glycoluril represented by formula 6 below and glycoluril represented by formula 8 below with paraformaldehyde or a formaldehyde solution, and radiating microwave to the resulting mixture in the presence of an acid catalyst, wherein the microwave is irradiated at a power level of 300 to 800 W:

(6)

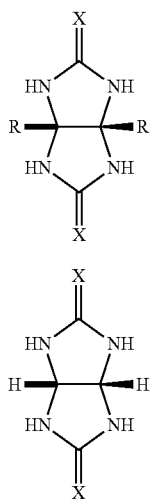

(8)

(7)

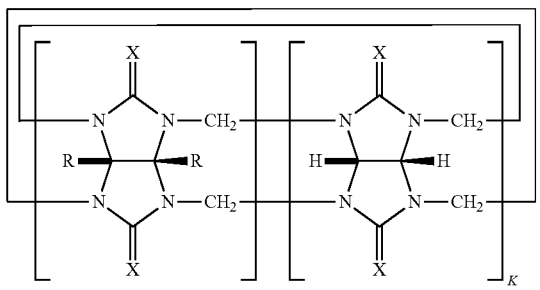

wherein R is selected from the group consisting of hydrogen, a substituted or unsubstituted alkyl group of C1-C30, a substituted or unsubstituted alkenyl group of C2-C30, a substituted or unsubstituted alkynyl group of C2-C30, a substituted or unsubstituted alkylcarboxyl group of C2-C30, a substituted or unsubstituted hydroxyalkyl group of C1-C30, a substituted or unsubstituted alkoxy group of C1-C30, a substituted or unsubstituted nitroalkyl group of C1-C30, —N(R')(R'') where R' and R'' are each independently hydrogen or an alkyl group of C1-C30, a substituted or unsubstituted cycloalkyl group of C5-C30, a substituted or unsubstituted heterocycloalkyl group of C2-C30, a substituted or unsubstituted aryl group of C6-C30, and a substituted or unsubstituted heteroaryl group of C2-C30;

X is O, S, or NH; and k is an integer from 4 to 7.

11. The process of claim 10, wherein the microwave is irradiated for 30 seconds to 10 minutes.

12. The process of claim 10, wherein the content of the glycoluril represented by the formula 8 is in the range from k to 1.2 k moles where k is an integer from 4 to 7 based on 1 mole of the disubstituted glycoluril represented by the formula 6.

13. The process of claim 10, wherein the content of the glycoluril represented by the formula 8 is in the range from 5 to 5.2 moles based on 1 mole of the disubstituted glycoluril represented by the formula 6.

14. The process of claim 10, wherein in the disubstituted cucurbituril represented by the formula 7, X is O, R is selected from the group consisting of 2-nitrophenyl group, 3-nitrophenyl group, 4-nitrophenyl group, 2-methoxyphenyl group, 3-methoxyphenyl group, 4-methoxyphenyl group, 2-aminophenyl group, 3-aminophenyl group, 4-aminophenyl group, 2-hydroxyphenyl group, 3-hydroxyphenyl group, and 4-hydroxyphenyl group, and k is an integer from 4 to 7.

15. The process of claim 10, wherein in the disubstituted glycoluril represented by the formula 6, X is O and R is selected from the group consisting of 2-nitrophenyl group, 3-nitrophenyl group, 4-nitrophenyl group, 2-methoxyphenyl group, 3-methoxyphenyl group, 4-methoxyphenyl group, 2-aminophenyl group, 3-aminophenyl group, 4-aminophenyl group, 2-hydroxyphenyl group, 3-hydroxyphenyl group, and 4-hydroxyphenyl group.

16. A process of preparing glycoluril represented by formula 2 below by irradiating microwave to a 1,2-diketone compound represented by formula 3 below and an urea compound represented by formula 4 below in the presence of an acid catalyst, wherein the microwave is irradiated at a power level of 300 to 1,600W:

(2)

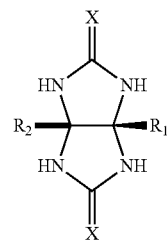

(3)

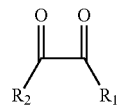

(4)

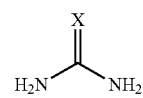

wherein X is O, $R_1$ and $R_2$ are hydrogen.

17. A process of preparing cucurbituril represented by formula 11 below by irradiating microwave to glycoluril represented by formula 10 below and paraformaldehyde or a formaldehyde solution in the presence of an acid catalyst, wherein the microwave is irradiated at a power level of 300 to 1,600W:

(11)

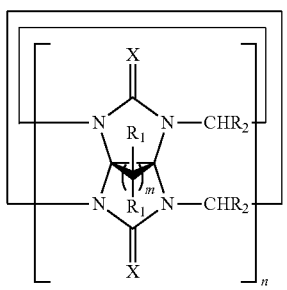

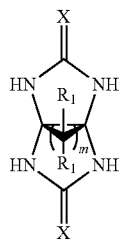

(10)

where X is O, S or NH; $R_1$ and $R_2$ are independently selected from the group consisting of hydrogen, alkyl groups of 1 to 30 carbon atoms, alkenyl groups of 1 to 30 carbon atoms, alkynyl groups of 1 to 30 carbon atoms, alkylthio groups of 1 to 30 carbon atoms, alkylcarboxyl groups of 1 to 30 carbon atoms, hydroxyalkyl groups of 1 to 30 carbon atoms, alkylsilyl groups of 1 to 30 carbon atoms, alkoxy groups of 1 to 30 carbon atoms, haloalkyl groups of 1 to 30 carbon atoms, nitro group, alkylamine groups of 1 to 30 carbon atoms, amine group, aminoalkyl groups of 1 to 30 carbon atoms, unsubstituted cycloalkyl groups of 5 to 30 carbon atoms, cycloalkyl groups of 4 to 30 carbon atoms with hetero atoms, unsubstituted aryl groups of 6 to 30 carbon atoms, and aryl groups of 6 to 30 carbon atoms with hetero atoms; and n and m are independently integers from 4 to 20 and from 1 to 7, respectively.

18. The process of claim 17, wherein the microwave is irradiated.

19. The process of claim 17, wherein the acid catalyst is at least one selected from the group consisting of hydrochloric acid, sulfuric acid, trifluoroacetic acid, methanesulfonic acid, phosphoric acid, tetrafluoroboric acid and toluenesulfonic acid.

20. A process of preparing cucurbituril represented by formula 1 below by irradiating microwave to glycoluril represented by formula 2 below and paraformaldehyde or a formaldehyde solution in the presence of an acid catalyst, wherein the microwave is irradiated at a power level of 300 W or 800 W:

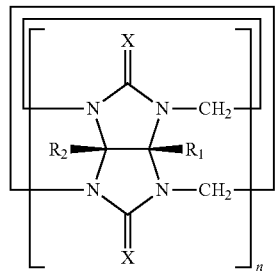

(1)

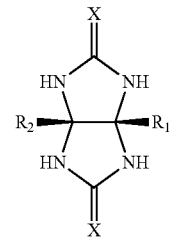

(2)

wherein X is O, S, or NH;

$R_1$ and $R_2$ are each independently selected from the group consisting of hydrogen, a substituted or unsubstituted alkyl group of C1-C30, a substituted or unsubstituted alkenyl group of C2-C30, a substituted or unsubstituted alkynyl group of C2-C30, a substituted or unsubstituted alkylcarboxyl group of C2-C30, a substituted or unsubstituted hydroxyalkyl group of C1-C30, a substituted or unsubstituted alkoxy group of C1-C30, a substituted or unsubstituted nitroalkyl group of C1-C30, —N(R')(R") where R' and R" are each independently hydrogen or an alkyl group of C1-C30, a substituted or unsubstituted cycloalkyl group of C5-C30, a substituted or unsubstituted heterocycloalkyl group of C2-C30, a substituted or unsubstituted aryl group of C6-C30, and a substituted or unsubstituted heteroaryl group of C2-C30; and n is an integer from 5 to 8 or 10.

* * * * *